United States Patent
Lunner et al.

(10) Patent No.: US 9,432,777 B2
(45) Date of Patent: Aug. 30, 2016

(54) HEARING DEVICE WITH BRAINWAVE DEPENDENT AUDIO PROCESSING

(71) Applicant: OTICON A/S, Smørum (DK)

(72) Inventors: Thomas Lunner, Smørum (DK); Fredrik Gustafsson, Linköping (SE)

(73) Assignee: OTICON A/S, Smorum (DK)

( * ) Notice: Subject to any disclaimer, the term of this patent is extended or adjusted under 35 U.S.C. 154(b) by 0 days.

(21) Appl. No.: 14/048,883

(22) Filed: Oct. 8, 2013

(65) Prior Publication Data

US 2014/0098981 A1   Apr. 10, 2014

Related U.S. Application Data

(60) Provisional application No. 61/710,796, filed on Oct. 8, 2012, provisional application No. 61/719,540, filed on Oct. 29, 2012.

(30) Foreign Application Priority Data

Oct. 8, 2012   (EP) .................................... 12187625
Oct. 29, 2012   (EP) .................................... 12190377

(51) Int. Cl.
*H04R 25/00*   (2006.01)
*G06F 3/01*   (2006.01)
(Continued)

(52) U.S. Cl.
CPC .............. *H04R 25/50* (2013.01); *H04R 25/70* (2013.01); *A61B 5/0484* (2013.01);
(Continued)

(58) Field of Classification Search
CPC ............ A61B 5/04845; A61B 5/1221; A61B 5/6815; A61B 5/6838; A61B 5/121; A61B 5/68; A61B 5/0484; G06F 3/015; H04R 25/50; H04R 25/70; H04R 2225/41; A61N 1/0541
USPC ................. 381/60, 314, 321, 323, 312, 320; 600/301, 544, 545
See application file for complete search history.

(56) References Cited

U.S. PATENT DOCUMENTS 8,271,075 B2 * 9/2012 Chuang ................ A61B 5/0478
600/383
2010/0246865 A1 * 9/2010 Suurballe ...................... 381/314
(Continued)

FOREIGN PATENT DOCUMENTS

FR   WO -02069327   * 9/2002   ............. G10L 21/02
FR   WO-02069327   * 9/2002   ............. G10L 21/02
(Continued)

OTHER PUBLICATIONS

Pasley et al, Reconstructing Speech from Human Auditory Cortex, www.plos.org. Pub Jan. 31, 2012; DOI.10.1371/journal.plos.1001251.*
(Continued)

*Primary Examiner* — Davetta W Goins
*Assistant Examiner* — Oyesola C Ojo
(74) *Attorney, Agent, or Firm* — Birch, Stewart, Kolasch & Birch, LLP

(57) ABSTRACT

A hearing device is adapted to be arranged on or at least partly implanted in an individual's head and comprises: an input unit providing an input audio signal; a signal processing circuit adapted to process the input audio signal; an output unit adapted to provide an audible signal to the individual; one or more electrodes adapted to detect electric brain potentials of the individual; and a brainwave measurement circuit adapted to determine one or more EEG signals from electric signals received from the one or more electrodes. The hearing device further comprises: a first spectrum analyzer determining first audio spectra; a reconstructor adapted to repeatedly reconstruct second audio spectra; a first correlator to determine coherence between the first and the second audio spectra; and a control unit adapted to alter said processing in dependence on the coherence.

34 Claims, 6 Drawing Sheets

(51) Int. Cl.
*A61B 5/0484* (2006.01)
*A61B 5/00* (2006.01)
*A61B 5/12* (2006.01)
*A61N 1/05* (2006.01)

(52) U.S. Cl.
CPC ........... *A61B 5/04845* (2013.01); *A61B 5/121* (2013.01); *A61B 5/68* (2013.01); *A61B 5/6815* (2013.01); *A61N 1/0541* (2013.01); *G06F 3/015* (2013.01); *H04R 2225/41* (2013.01)

(56) References Cited

U.S. PATENT DOCUMENTS

| | | | | |
|---|---|---|---|---|
| 2010/0246866 | A1* | 9/2010 | Swain et al. | 381/315 |
| 2010/0248025 | A1* | 9/2010 | Kimura et al. | 429/207 |
| 2010/0250242 | A1* | 9/2010 | Li | 704/200.1 |
| 2010/0280338 | A1* | 11/2010 | Chou | A61B 5/6838 600/301 |
| 2011/0028827 | A1* | 2/2011 | Sitaram | A61B 5/0059 600/410 |
| 2012/0176515 | A1* | 7/2012 | Teo | H04N 5/23238 348/239 |
| 2012/0177233 | A1* | 7/2012 | Kidmose | A61B 5/04845 381/314 |
| 2013/0235399 | A1* | 9/2013 | Conlon | G06K 15/16 358/1.12 |
| 2013/0301061 | A1* | 11/2013 | Conlon | G06F 3/1208 358/1.2 |

FOREIGN PATENT DOCUMENTS

| | | | |
|---|---|---|---|
| JP | 2010-82375 A | 4/2010 | |
| JP | 2010082375 | * 4/2010 | ............ A61F 11/00 |
| JP | 20100082375 | * 4/2010 | ............ A61F 11/00 |
| WO | WO-02069327 | * 9/2002 | ............ G10L 21/02 |
| WO | WO 2011/006681 A1 | 1/2011 | |
| WO | WO 2012/095171 A1 | 7/2012 | |
| WO | WO 2012/103940 A1 | 8/2012 | |

OTHER PUBLICATIONS

European Search Report for EP 12187625.4 dated Jan. 23, 2013.

* cited by examiner

HEARING DEVICE WITH BRAINWAVE DEPENDENT AUDIO PROCESSING

TECHNICAL FIELD

The present invention relates to a hearing device with brainwave dependent audio processing. More specifically, the present invention relates to a hearing device such as e.g. a hearing aid, a listening device, an active ear-protection device, an earphone or a headset, which has a sensor for measuring brainwaves of the hearing device's user and which adapts its audio processing in dependence on the measured brainwaves.

The invention may e.g. be useful in applications such as a hearing aid for compensating for a hearing-impaired person's loss of hearing capability, a listening device for augmenting a normal-hearing person's hearing capability, an active ear-protection device for protecting a person's auditory system, an earphone for conveying electronic audio signals to the user or a headset for communicating with another person.

BACKGROUND ART

A common challenge in the technical field of hearing devices is to improve the ability of the hearing-device user to focus attention on a specific speaker in a sound environment with two or more speakers, i.e. to ameliorate the so-called "cocktail-party" effect.

WO2008097201A1 [Guan et al.; 2008] deals with a system and method for processing brain signals in a Brain Computer Interface (BCI) system. The method of processing brain signals in a BCI system comprises the steps of processing the brain signals for control state detection to determine if a subject intends to use the BCI system; and processing the brain signals for command recognition if the control state detection method determines that the subject intends to use the BCI system.

EP2200342A1 [Husung et al.; 2010] deals with a hearing aid comprising a hearing aid component, a brainwave signal receiver configured to receive brainwave signals, and a hearing aid controller configured to control the hearing aid component dependent on the detected brainwave signals.

JP2010082375A [Higuchi; 2010] describes a sound signal processor comprising a brain waveform measuring part, a correlation calculating part for determining a correlation value of each waveform of a plurality of sound signals and a measured brain waveform. An attentively hearing sound specifying part specifies the sound signal having the largest correlation value among the plurality of sound signals as an attentively hearing sound. A weighting and synthesizing part performs weighting so that the sound signal specified as the attentively hearing sound is emphasized more than the other sound signals, and then the plurality of sound signals are synthesized. A sound output part outputs the sound signal synthesized by the weighting and synthesizing part to a headphone or a speaker.

International patent application WO 2011/006681 A1 [Kidmose et al.; 2011] discloses a hearing aid comprising means for modifying the operation of the hearing aid in response to electric signals, such as brainwaves, detected by means of electrodes arranged on and/or in a surface of a part of the hearing aid. The hearing aid may comprise feature extraction means for extracting features from the electric signals and classification means for classifying the extracted features. Examples are given on how brainwave signals may differ when the hearing-aid user focuses his attention either to the music or to the speech in a mixed signal comprising both. It is suggested that when it can be determined to which part of an acoustic image the user pays attention, this information may be used to enable adaptation of the hearing aid to obtain optimum intelligibility of the particular part of the acoustic image. However, details regarding how to distinguish between multiple speakers or how to use such information to adapt the hearing aid are not disclosed.

In an article in Nature, volume 485, p. 233-236, 2012 ('Selective cortical representation of attended speaker in multi-talker speech perception') N. Mesgarani and E. F. Chang disclose experimental results that indicate that speech spectrograms reconstructed based on high-gamma cortical responses to acoustic signals comprising a mixture of speakers reveal the salient spectral and temporal features of the attended speaker—as if the subject were listening to that speaker alone. The cortical responses were measured using implanted high-density electrode arrays. The article does not disclose any details as to how this new knowledge could be used, e.g. in hearing devices.

DISCLOSURE OF INVENTION

It is an object of the present invention to provide a hearing device, which may improve the ability of the hearing-device user to focus attention on a specific speaker in a sound environment with two or more audio sources, e.g. comprising two different speakers.

This and other objects of the invention are achieved by the invention defined in the accompanying independent claims and as explained in the following description. Further objects of the invention are achieved by the embodiments defined in the dependent claims and in the detailed description of the invention.

In the present context, a "hearing device" refers to a device, such as e.g. a hearing aid, a listening device or an active ear-protection device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A "hearing device" further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing device may comprise a single unit or several units communicating electronically with each other.

More generally, a hearing device comprises an input transducer for receiving an acoustic signal from an user's surroundings and providing a corresponding input audio signal and/or a receiver for electronically receiving an input audio signal, a signal processing circuit for processing the input audio signal and an output unit (or means) for providing an audible signal to the user in dependence on the processed audio signal. In some hearing devices, an amplifier may constitute the signal processing circuit. In some hearing devices, the output means may comprise an output transducer, such as e.g. a loudspeaker for providing an air-borne acoustic signal or a vibrator for providing a structure-borne or liquid-borne acoustic signal. In some hearing devices, the output means may comprise one or more output electrodes for providing electric signals.

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A "hearing system" refers to a system comprising one or two hearing devices, and a "binaural hearing system" refers to a system comprising one or two hearing devices and being adapted to cooperatively provide audible signals to both of the user's ears. Hearing systems or binaural hearing systems may further comprise "auxiliary devices", which communicate with the hearing devices and affect and/or benefit from the function of the hearing devices. Auxiliary devices may be e.g. remote controls, audio gateway devices, mobile phones, public-address systems, car audio systems or music players. Hearing devices, hearing systems or binaural hearing systems may e.g. be used for compensating for a hearing-impaired person's loss of hearing capability, augmenting or protecting a normal-hearing person's hearing capability and/or conveying electronic audio signals to a person.

A Hearing Device:

In a first aspect, an object of the invention is provided by a hearing device adapted or configured to be arranged (at least partly) on an individual's head or at least partly implanted in an individual's head and comprising:

an input unit providing one or more input audio signals;
a signal processing circuit adapted to process at least one of said one or more input audio signals to provide a processed audio signal;
one or more electrodes adapted to detect electric brain potentials of the individual; and
a brainwave measurement circuit adapted to determine one or more brainwave signals from electric signals received from the electrode(s);
a first correlator adapted to repeatedly determine a first correlation measure between at least one of said one or more input audio signals or a processed version thereof and at least one of said one or more brainwave signals; and
a control unit adapted to alter said processing in dependence on the first correlation measure.

In a second aspect, an object of the invention is provided by a hearing device adapted or configured to be arranged (at least partly) on an individual's head or at least partly implanted in an individual's head and comprising:

an input unit providing one or more input audio signals;
a signal processing circuit adapted to process at least one of said one or more input audio signals to provide a processed audio signal;
one or more electrodes adapted to detect electric brain potentials of the individual; and
a brainwave measurement circuit adapted to determine one or more brainwave signals from electric signals received from the electrode(s);
a model unit adapted to repeatedly determine a model providing a similarity measure indicating a degree of similarity of at least one of said one or more input audio signals or a processed version thereof and at least one of said one or more brainwave signals; and
a control unit adapted to alter said processing in dependence on the similarity measure.

In an embodiment, the model is a causal model. In an embodiment, the model is a causal model of the transfer of an audio signal to the brain signal(s). In an embodiment, the model has a memory. Preferably, the memory is optimized to the application in question (to be able to handle a delay in a brain signal in response to an input audio signal). Preferably, the memory of the model is optimized to the individual wearing the hearing device.

In an embodiment, the model comprises a transfer function $$H(q) = \frac{B(q)}{A(q)} = \frac{b_0 + b_1 q^{-1} + \ldots + b_n q^{-n}}{1 + a_1 q^{-1} + \ldots + a_n q^{-n}}$$

where $q^{-1}$ denotes the shift operator, $q^{-1}s[n]=s[n-1]$, and n is a time index.

The idea is to estimate this transfer function from data according to the model $$A(q)s_i[n]=B_j(q)e_j[n]+\text{res}[n]$$

where res[n] is "noise" (model residual).

In an embodiment, the hearing device further comprises a first spectrum analyser adapted to repeatedly determine first audio spectra of at least one signal from the group of signals consisting of said one or more input audio signals and the processed audio signal, a reconstructor adapted to repeatedly reconstruct second audio spectra from the one or more brainwave signals (e.g. EEG signals), and wherein the model unit is configured to repeatedly determine the similarity measure between the first and second audio spectra.

In an embodiment, the determination of the similarity measure is optimized with respect to time consumption. In an embodiment, the hearing device is configured to apply a maximum time ($t_{i,max}$) to determine a resulting similarity measure for a given input audio signal. In an embodiment, the hearing device is configured to apply a maximum time ($t_{max}$) to determine a resulting similarity measure for a given input audio signal. In an embodiment, the hearing device is configured to identify one of the input audio signals that has the highest probability of being a target signal for the individual wearing the hearing device within a predefined maximum time (Tmax). In an embodiment, the control unit is configured to identify the input audio signal (at a given point in time) that has the largest resulting similarity measure within a predefined maximum time (Tmax). In an embodiment, the hearing device is configured to provide that Tmax is smaller than 100 s, such as smaller than 30 s, such as smaller than 10 s. In general, $(t_{i,max}) < (t_{max}) < (T_{max})$.

In an embodiment, the hearing device further comprises an output unit for receiving the processed audio signal. In an embodiment, the output unit is adapted to avail the processed output signal for further processing in the hearing device or for transmitting it (e.g. wirelessly) to another device, e.g. for further processing or for being presented to another user.

In an embodiment, the hearing device comprises one or more voice activity detectors applied to one or more of the input audio signals to detect periods of time, and possibly frequency bands, where the signals in question comprise a speech signal component and where not. This may simplify the required processing for determining the similarity measure.

In an embodiment, the output unit is adapted to process (e.g. convert) said processed output signal to provide stimuli to the individual perceived by the individual as an audible signal.

In a third aspect an object of the invention is provided by a hearing device adapted or configured to be arranged (at least partly) on an individual's head or at least partly implanted in an individual's head and comprising: an input unit providing one or more input audio signals; a signal processing circuit adapted to process at least one of said one or more input audio signals to provide a processed audio signal; an output unit adapted to provide an audible signal to the individual in dependence on the processed audio signal; one (e.g. two) or more electrodes adapted to detect electric brain potentials of the individual; and a brainwave measurement circuit adapted to determine one or more EEG signals from electric signals received from the electrode(s). The hearing device further comprises: a first spectrum analyser adapted to repeatedly determine first audio spectra of at least one signal from the group of signals consisting of said one or more input audio signals and the audible signal; a reconstructor adapted to repeatedly reconstruct second audio spectra from the one or more EEG signals; a first correlator adapted to repeatedly determine a first correlation measure (e.g. coherence) between the first and the second audio spectra; and a control unit adapted to alter said processing in dependence on the first correlation measure (e.g. coherence).

In an embodiment, the one or more electrodes adapted to detect electric brain potentials comprises a multitude of electrodes, e.g. two or more, such as three or more, e.g. five or more electrodes. In an embodiment, the one or more electrodes comprises a reference electrode. In an embodiment, the potentials of the other electrodes are referred to the reference electrode.

In an embodiment, the first correlator is configured to determine a correlation $c_{ij}$ between a given input audio signal $s_i$ and each of the brainwave signals $e_j$ (j=1, 2, ..., J) received from the brainwave measurement circuit. In an embodiment, the first correlator is configured to determine a resulting correlation measure $CM_i$ based on said J correlation values $c_{ij}$ of the $i^{th}$ input audio signal $s_i$.

In an embodiment, the first correlator is configured to determine a correlation $c_{ij}$ between each of the input audio signal $s_i$ (i=1, 2, ..., N) and each of the brainwave signals $e_j$ (j=1, 2, ..., J) received from the brainwave measurement circuit. In an embodiment, the first correlator is configured to determine a resulting correlation measure $CM_i$ based on said J correlation values $c_{ij}$ of the $i^{th}$ input audio signal $s_i$ for each of the input audio signal $s_i$ (i=1, 2, ..., N).

In an embodiment, the resulting correlation measure $CM_i$ for input audio signal $s_i$ (based on the current brainwave signals $e_j$) is determined as the maximum correlation value $c_{ij}$ (j=1, 2, ..., J). In an embodiment, the resulting correlation measure $CM_i$ is determined as the average of the J correlation values $c_{ij}$. Other schemes for determining resulting correlation measure $CM_i$ can be used, e.g. a weighted average (e.g. giving a low weight to correlation values relating to brainwave signals with a relatively low dynamic range).

Preferably, the control unit is configured to identify one of the input audio signals that has the highest probability of being a target signal for the individual wearing the hearing device. In an embodiment, the control unit is, alternatively or additionally, configured to identify an input audio signal that has a low probability of being a target signal for the individual wearing the hearing device.

In an embodiment, the control unit is configured to identify the input audio signal $s_i$ that has the largest resulting correlation measure $CM_i$.

In an embodiment, the resulting correlation measure for a given input audio signal $s_i$ is based on one or more of the correlation values $c_{ij}$. In an embodiment, the control unit is configured to identify the input audio signal $s_q$ as the one for which one or more of the correlation values $c_{qj}$ (e.g. $c_{qj'}$, i.e. e.g. one correlation value corresponding to j=j') is/are larger than the corresponding correlation values $c_{ij}$ (e.g. $c_{ij'}$) for all other input audio signals i≠q.

In an embodiment, the input unit comprises a number (M) of input transducers (e.g. microphones, e.g. forming part of a microphone array), each configured to convert an input sound of a sound field surrounding the hearing device to an electric input signal. Preferably, the input unit comprises a source separation unit for separating one or more sound sources s (s=1, 2, ..., N, where N is the current number of audio sources, e.g. talkers) in the sound field based on electric input signals, and providing respective separated input audio signals $X_s$, from said one or more sound sources s.

In an embodiment, input unit comprises a number of weighting units adapted for providing a number of directional signals as input audio signals.

In an embodiment, the input unit comprises a number of wireless receivers for receiving at least some of the input audio signals. In an embodiment, all input audio signals of the hearing device are received by respective wireless receivers. In an embodiment, the wirelessly received signals are assumed to be 'clean' signals, e.g. picked up by a microphone in close proximity of a speakers mouth and/or received from a telephone, a headset or the like.

A correlation measure indicating a degree of similarity of two signals is in the present context taken to include a mathematical correlation between electrical representations of the two signals. In an embodiment, the correlation measure is based on the calculation of a correlation coefficient, e.g. Pearson's correlation coefficient. Person's correlation coefficient $\rho_{xy}$, for two signals x and y is defined as the covariance cov(x,y) divided by the product of the individual standard deviations $\sigma_x$ og $\sigma_y$.

In an embodiment, the correlation measure $c_{ij}$ is based on the covariance between a speech signal $s_i$ and each brainwave signal $e_j$:

$$c_{ij} = s_i^T e_j.$$

In an embodiment, the resulting correlation measure $CM_i$ for input audio signal i is a weighted sum of the individual correlation values $$CM_i = c_i = \sum_j w_j c_{ij}$$

In an embodiment, the correlation measure $c_{ij}$ is based on cross-correlation to take account of the input audio signal and the brainwave signals NOT necessarily being synchronized in time (on the scale of relevance for the signal processing of the hearing device, i.e. e.g. relative to a time between audio samples). In an embodiment, cross correlation between two signals (input audio and brainwave signals) is maximized with respect to a delay (lag) between the two signals.

In a preferred embodiment, the correlation measure is (mathematical) coherence. The term 'coherence' is a term from signal processing and used in the following. The term is intended to have its normal meaning (to indicate a relation between two signals, e.g. to estimate a power transfer between an input signal and an output signal of a linear system). The coherence between two signals x(t) and y(t), t being time, is defined by $$\text{coherence}_{xy}(f) = \frac{|P_{xy}(f)|^2}{P_{xx}(f) \cdot P_{yy}(f)}$$

where $P_{xy}$ denotes the cross-spectral density between x(t) and y(t), and $P_{xx}$ and $P_{yy}$ denote the auto-spectral density of x(t) and y(t), respectively, and f is frequency. The coherence function $\text{coherence}_{xy}(f)$ has values between 0 and 1 and estimates the extent to which y(t) may be predicted from x(t) by an optimum linear least squares function (t being time), cf. e.g. the entry on coherence in Wikipedia relating to signal processing.

In the present context, x(t) may be a brainwave signal and y(t) a target sound signal (e.g. a male voice) hiding in (or forming part of) the input signal (y(t)+w(t), where w(t) represents another voice, e.g. a female voice, noise, or another sound. The coherence function $\text{coherence}_{xy}(f)$ thus gives an estimate of the extent to which the male voice (target sound, y(t)) can be predicted from the brainwave signal (x(t)).

In an embodiment, the correlation measure is based on computationally simpler methods of estimating a correlation between the two signals in question, e.g. by operating only on parts of the signals in question, e.g. an envelope (e.g. as given by a Hilbert transform or as provided by a low pass filtering).

The term 'an output unit adapted to provide an audible signal to the individual' is in the present context taken to mean an output unit adapted to provide output stimuli configured to be perceived by a user as an audible signal (sound). The output unit (or output means) may e.g. comprise one or more of a vibrator (of a bone anchored hearing device), a loudspeaker (of an air conduction hearing device), and one or more electrodes (of a cochlear implant hearing device).

The 'one or more electrodes adapted to detect electric brain potentials of the individual' may be surface electrode (s) adapted for being located on the head of the user, e.g. in the ear, such as in the ear canal, the electrode(s) being e.g. arranged on a housing of the hearing device. Alternatively or additionally, the 'one or more electrodes adapted to detect electric brain potentials of the individual' (or one or more of them) may be fully or partially implanted in the users' head (e.g. as described above for the output electrodes).

A Binaural Hearing System:

In a further aspect, a binaural hearing system comprising first and second hearing assistance device as described above, in the 'detailed description of embodiments', and in the claims, is moreover provided.

The binaural hearing system is adapted to establish a communication link between the first and second hearing devices to provide that information (e.g. data, such as control signals, status signals, audio signals) can be exchanged or forwarded from one to the other.

In an embodiment, binaural hearing system is configured to exchange audio signals (e.g. one or more of the input audio signals and/or the signals received from the audio sources e.g. via an input transducer such as a microphone or a wireless receiver) and control signals between the two hearing devices via appropriate antenna and transceiver circuitry configured to establish a wireless link. This allows the system to identify which of the currently received signals—be it acoustically propagated or wirelessly received signals, be it received by the first and/or second hearing device—that the user wishes to focus on (e.g. music from an entertainment device or speech from a TV or telephone audio input or acoustic inputs from the environment).

In an embodiment, the binaural hearing system comprises an auxiliary device, e.g. an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing assistance device. In an embodiment, the auxiliary device is or comprises a SmartPhone. In an embodiment, the auxiliary device is or comprises a remote control for controlling functionality and operation of the hearing assistance device(s). In an embodiment, the function of a remote control is implemented in a SmartPhone, the SmartPhone possibly running an APP allowing to control the functionality of the audio processing device via the SmartPhone (the hearing assistance device(s) comprising an appropriate wireless interface to the Smart-Phone, e.g. based on Bluetooth or some other standardized or proprietary scheme).

A Method of Operating a Hearing Device:

In an aspect, a method of operating a hearing device is provided. The method comprises:
  providing one or more input audio signals;
  processing at least one of said one or more input audio signals to provide a processed audio signal;
  detecting one or more electric brain potentials of the individual;
  determine one or more brainwave signals from the electric brain potentials;
  repeatedly determining a similarity measure between at least one of said one or more input audio signals or a processed version thereof and at least one of said one or more brainwave signals; and
  controlling said processing of at least one of said one or more input audio signals in dependence on the similarity measure.

It is intended that some or all of the structural features of the device described above, in the 'detailed description of embodiments' or in the claims can be combined with embodiments of the method, when appropriately substituted by a corresponding process feature and vice versa. Embodiments of the method have the same advantages as the corresponding device.

In an embodiment, the control of the processing comprises identifying the input audio signal that has the highest probability of being a target signal for the individual wearing the hearing device. In an embodiment, the control of the processing, alternatively or additionally, comprises identifying an input audio signal that has a low probability of being a target signal for the individual wearing the hearing device.

In an embodiment, the method comprises a learning mode, wherein a target signal is known (agreed on in advance of activating the method).

In the following description of the learning mode, it is assumed that a controlled experiment is conducted, wherein the listener tries to focus on one particular sound source, e.g. speaker number 1 (signal $s_1(t)$). It is further assumed that the brainwave signals $e_j(t)$ are EEG-signals (but this is not important for the general aspects of the method).

The goal is to find a pattern in the EEG signals $e_j(t)$ (j= 1, . . . , J) that correlates strongly to $s_1(t)$, and much less to $s_i(t)$, $i \neq 1$.

In an embodiment, a causal model of the transfer of an audio signal to the brain signal(s) is used to determine the similarity measure. In an embodiment, the model has a memory. Preferably, the memory is optimized to the application in question (to be able to handle a delay in a brain signal in response to an input audio signal). Preferably, the memory of the model is optimized to the individual wearing the hearing device. In an embodiment, the model is trained during a training phase, where the learning mode is activated (the hearing device is in a learning mode).

In an embodiment, the model is trained on a number of different voices (to provide that the model is better suited for identifying such voices in a sound field comprising a mixture of voices (and possibly other (e.g. noise) sounds). In an embodiment, the model is trained on a particular voice (that is denoted the target input audio signal) in a sound field comprising a mixture of the target voice and one or more other voices, and possibly additional noise at different levels.

In an embodiment, the similarity measure is determined by analysis of the input audio signals and the brainwave signals in the (time-)frequency domain in the learning mode, and wherein the similarity measure is determined by analysis in the time domain in a normal mode of operation of the hearing device.

As used herein, the singular forms "a", "an", and "the" are intended to include the plural forms as well (i.e. to have the meaning "at least one"), unless expressly stated otherwise. It will be further understood that the terms "has", "includes", "comprises", "having", "including" and/or "comprising", when used in this specification, specify the presence of stated features, integers, steps, operations, elements and/or components, but do not preclude the presence or addition of one or more other features, integers, steps, operations, elements, components and/or groups thereof. It will be understood that when an element is referred to as being "connected" or "coupled" to another element, it can be directly connected or coupled to the other element, or intervening elements may be present, unless expressly stated otherwise. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF THE DRAWINGS

The invention will be explained in more detail below in connection with preferred embodiments and with reference to the drawings in which.

Figure 1:
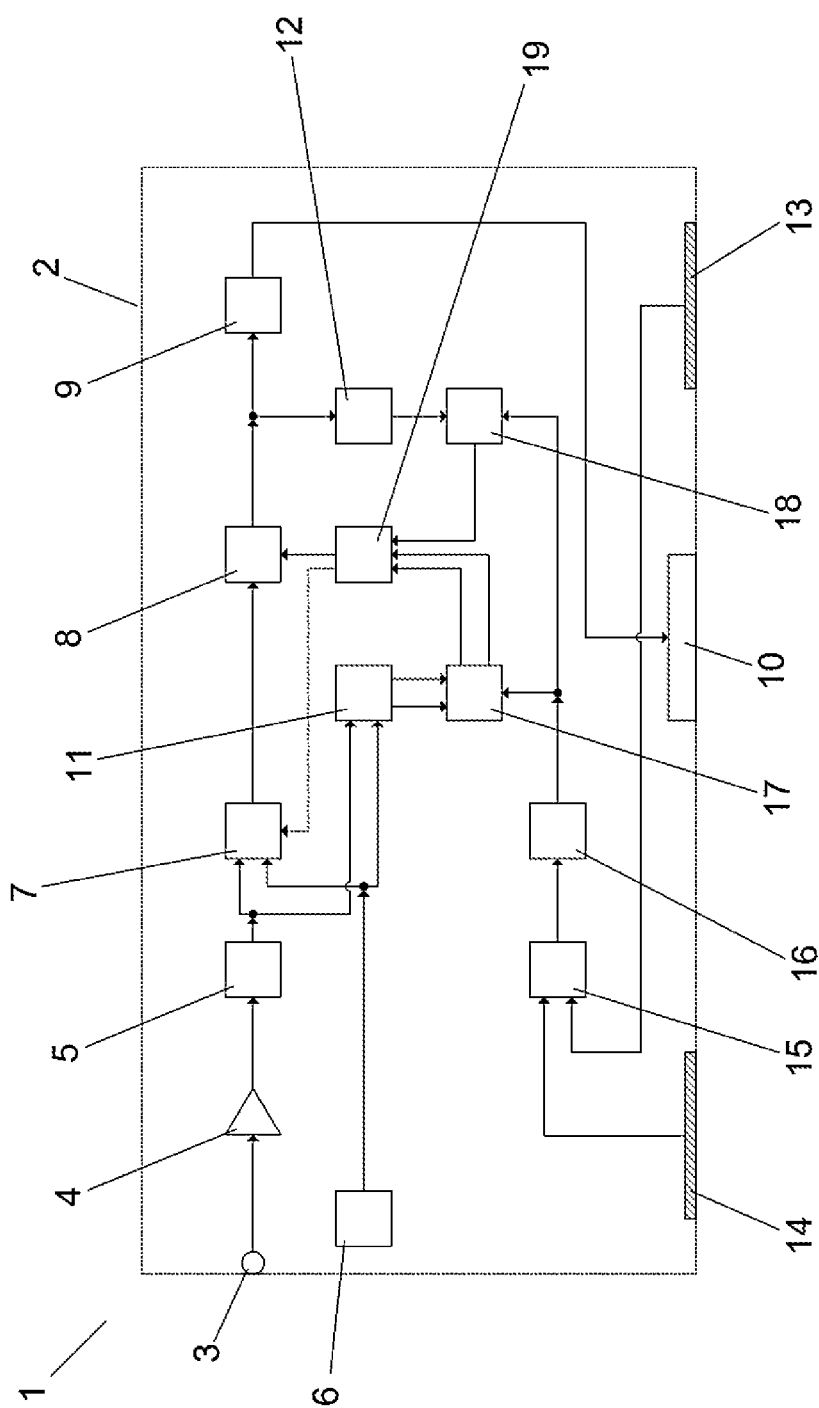
FIG. 1 shows a first embodiment of a hearing device according to the invention.

The figures are schematic and simplified for clarity, and they just show details, which are essential to the understanding of the invention, while other details are left out.

Further scope of applicability of the present invention will become apparent from the detailed description given hereinafter. However, it should be understood that the detailed description and specific examples, while indicating preferred embodiments of the invention, are given by way of illustration only, since various changes and modifications within the scope of the invention will become apparent to those skilled in the art from this detailed description.

MODE(S) FOR CARRYING OUT THE INVENTION

Theoretical Considerations

The cocktail party problem occurs when several people, i=1, . . . , N, are emitting speech signals $s_i(t)$ at the same time, and the listener receives the sum of them $$s(t) = \sum_{i=1}^{N} s_i(t)$$

An assumption is that the listener tries to single out one of them, say $s_1(t)$, and the technical challenge is to find out which speech signal it is, based on extraneous sensor measurements, here brainwave signals, e.g. EEG signals, $e_j(t)$, j=1, . . . , J, where J is the number of brainwave signals (e.g. originating from J electrodes located on and/or in the body of the user). We assume that the algorithm has access to the individual sound sources $s_i[mT_s]$ (e.g. using a microphone array and a source separation algorithm) sampled at frequency $f_s=1/T_s$, where $T_s$ is the time between each audio sample, and the brainwave (e.g. EEG) signals $e_k[mT_e]$ sampled at frequency $f_e=1/T_e$, where $T_e$ is the time between each brainwave sample. The parameter m is an (integer) index indicating that the signals are assumed to be known at consecutive multipla of $T_s$ (and $T_e$), m=0, 1, 2, . . . M.

The information can be summarized in the two matrices, speech signal matrix $S=[s_1, \ldots, s_N]$ and brainwave signal matrix $E=[e_1, \ldots, e_J]$.

Microphone array techniques are e.g. discussed in chapter 7 of [Schaub, 2008] Schaub, A. Digital Hearing Aids. Thieme Medical Publishers, 2008. Blind source separation techniques are described in a variety of sources, e.g. in [Bell and Sejnowski, 1995] (Bell, A. J. and Sejnowski, T. J. *An information maximisation approach to blind separation and blind deconvolution*. Neural Computation, Vol. 7(6), pp. 1129-1159, 1995).

Exemplary Parameter Values:

Typically, the sampling time $T_e$ is larger than $T_s$, such as more than 10 times larger. The number of speakers N can in principle be any number. Preferably, however, the number of speech signals N is smaller than 5, e.g. in the range between 2 and 4. Likewise, the number of brainwave signals J (e.g. provided by individual electrodes) can in principle be any number. Preferably, however, J is larger than 2, e.g. larger than 4, e.g. larger than 10, such as larger than 50, e.g. in the range between 100 and 200.

Exemplary values of the parameters are N=2, J=128, $T_s$=1/8192 and $T_e$=1/250.

Approaches for Learning:

In the following, it is assumed that a controlled experiment is conducted, wherein the listener tries to focus on speaker number 1 (signal $s_1(t)$). It is further assumed that the brainwave signals $e_j(t)$ are EEG-signals.

The goal is to find a pattern in the EEG signals $e_j(t)$ (j= 1, ..., J) that correlates strongly to $s_1(t)$, and much less to $s_i(t)$, i≠1.

A. Pre-Processing and Resampling the Speech Signal:

Since the sample rates of the speech signals $s_i(t)$ and the EEG signals $e_j(t)$ are different, and EEG measures energy rather than amplitude as in the speech signal, some preprocessing is appropriate. When operating in the time domain, the most natural approach is to square the speech signal to obtain the temporal energy ($|s_i(t)|^2$), and then to lowpass filter and decimate it to get the same 'sample rate' as the EEG signal. The same effect can be obtained when operating in the frequency domain, e.g. by squaring an FFT-representation ($S_i(k,n)$) of the speech signal ($|S_i(n,k)|^2$) (where n is a time index and k is a frequency index), put high frequencies to zero, and then apply the inverse FFT to the result. There are also other solutions with similar effects. We call the obtained (preprocessed) speech signal matrix S' (which after the above preprocessing has the same number of rows as the EEG signal matrix E). Here, S' is a matrix where a particular column represents a particular speech signal, and where each row corresponds to one time instant.

B. Frequency and Time Selective Windowing:

The next step is to focus on parts of the time and frequency domain where there is a clear relation between S' and E.

First, there is typically one or more frequency bands where the EEG signal is better correlated with the speech signal $s_1(t)$ of interest (than in the rest of the frequency bands). Thus, a frequency selective filter can be applied to the columns of both S' and E. If the union of the pass bands is much smaller than (e.g. smaller than 0.5 times, such as smaller than 0.1 times) the sampling frequency from the previous step, then down-sampling the signal (e.g. picking out every 10 sample), relying on the positive effects of aliasing, is plausible to reduce the amount of data. The coherence function is a useful tool to find this correlation in the frequency domain.

Second, the speaker providing speech signal $s_1(t)$ is typically not active all of the time. A time selective window can thus be applied to pick out time intervals (rows correspond to time here) in S' and E.

C. Modeling

In the following, a number of possible approaches for determining a correlation measure between the speech signals and the brainwave (e.g. EEG) signals (first and second audio signals, respectively):

Correlation.

The covariance between each speech signal and each EEG signal can be used to measure correlation:

$$C_{ij} = s_i^T e_j$$

One can hope to find a high correlation for at least one j (the $j^{th}$ EEG-signal) to speaker 1, for which $c_{1j} > c_{ij}$ for all i>1. One might also try to combine the different correlations, for instance a weighted sum $$c_i = \sum_j w_j c_{ij}$$

to make use of all EEG signals.

Cross-Correlation.

The drawback with correlation is that it assumed that both S and E are synchronized in time, which is hardly the case. Cross correlation delays one of the sequences before the correlation is computed. This creates an extra degree of freedom, so one has to maximize cross correlation with respect to this lag.

Canonical correlation analysis (CCA) computes the correlation between the linearly transformed signals $W_S S$ and $W_E E$. The weighting matrices $W_S$ and $W_E$ are computed from the covariance function of S and E.

A drawback of correlation based approaches is that they compare sample by sample, and they would fail if there is a strong dynamical relationship between S and E. The advantage of CCA is that it catches possible dynamics in the weighting matrices. However, this weighting does not correspond to physics. For instance, it is non-causal, with the consequence that the brain can foresee that there is a person who will speak in the future. It also has an extremely long memory that stretches over the whole set of learning data, meaning that the brain can react on speech that was spoken several minutes ago.

It is an object of the present disclosure to identify a model of higher physical relevance. The model should preferably be causal from speech to EEG, and have a reasonably long memory. One such class of models consists of transfer functions $$H(q) = \frac{B(q)}{A(q)} = \frac{b_0 + b_1 q^{-1} + \ldots + b_n q^{-n}}{1 + a_1 q^{-1} + \ldots + a_n q^{-n}}$$

Where $q^{-1}$ denotes the shift operator, $q^{-1} s[k] = s[k-1]$. The idea is to estimate this transfer function from data according to the model $$A(q)s_1[k] = B(q)e_j[k] + n[k]$$

where n[k] is "noise" (model residual). All EEG signals can be included in the model by using different sets of numerator polynomials $B_i(q)$ for each one, $$A(q)s_1[k] = \sum_{j=1}^{J} B_j(q) e_j[k] + n[k]$$

There are many plausible model structures with similar definitions. The advantage with the one above is that it is linear in the parameters, so the least squares criterion provides an analytic solution for the parameters $\theta=(a_1, \ldots, a_n, b_{11}, \ldots, b_{J,n})$, defined as $$\hat{\theta} = \arg\min_{\theta} \sum_{k=1}^{N} (s_1[k] - H(q)E[k])^2$$

If we now define $$V_i = \frac{\sum_{k=1}^{N} (s_i[k] - H(q;\hat{\theta})E[k])^2}{\sum_{k=1}^{N} s_i^2[k]}$$

Apparently, $0 \leq V_1 \leq 1$. The model is good if $V_1 \ll 1$ (e.g. <0.1). The model is useful for classification if $V_1 \ll V_j$, for j>1.

On-Line Classification:

If $\theta$ is consistently estimated for different situations, but for each individual, it can also be used on-line. The normalized loss function (cf. $V_i$ above) can be computed for each i, and the speech signal corresponding to the smallest one is selected. The transfer function is here a parametric tool for assessing correlation between EEG and audio signals. A stable transfer function includes automatically the physical constraints of causality and decaying memory in the correlation structure.

EXAMPLES

The first embodiment of a hearing device 1 shown in FIG. 1 comprises a housing 2, a microphone 3, a preamplifier 4, a digitiser 5, a wireless receiver 6, a mixer 7, a signal processor 8, a power amplifier 9, a vibrator 10, an input spectrum analyser 11, an output spectrum analyser 12, a first surface electrode 13, a second surface electrode 14, a brainwave measurement circuit 15, a reconstructor 16, an input correlator 17, an output correlator 18 and a control unit 19. The hearing device 1 is preferably powered by means of a battery or an accumulator (not shown) in the housing 2.

The housing 2 is adapted to be arranged in an operating position on the head of a user of the hearing device 1, e.g. by means of an elastic band or a spring. The microphone 3 is arranged to receive an acoustic input signal from the user's surroundings when the housing 2 is in the operating position and is adapted to provide a microphone signal to the preamplifier 4 in dependence on the acoustic input signal. The preamplifier 4 is adapted to amplify the microphone signal and to provide the amplified microphone signal to the digitiser 5, which is adapted to digitise the amplified microphone signal and provide a corresponding first digital input audio signal.

The wireless receiver 6 is adapted to receive a wireless communication signal, such as e.g. an inductive signal, a radio-frequency (RF) signal or an optical signal, from a further device and to provide a second digital input audio signal in dependence on the received wireless communication signal. The microphone 3, the preamplifier 4, the digitiser 5 and the wireless receiver 6 thus function as input means that provide input audio signals. The input means may comprise further microphones 3, preamplifiers 4 and/or digitisers 5 providing respective further input audio signals in order to allow e.g. direction-dependent processing of the received acoustic signals.

The mixer 7 is connected to receive the first and second digital input audio signals and is adapted to provide a combined audio signal comprising a linear combination of the first and second digital input audio signals in dependence on a control signal received from the control unit 19. The signal processor 8 is adapted to modify the combined audio signal in accordance with the purpose of the hearing device 1, e.g. to improve or augment the hearing capability of the user and/or to amplify or convey a received audio signal to the user. The power amplifier 9 is connected to receive the modified audio signal and is adapted to provide a corresponding amplified output signal to the vibrator 10, which is arranged to transmit a structure-borne acoustic output signal to the user in dependence on the amplified output signal when the housing 2 is in the operating position. The power amplifier 9 preferably comprises a pulse-width modulator or another type of digital-to-analog converter in order to provide the amplified output signal as an analog signal to the vibrator 10. Vibrators for bone anchored hearing devices are known in many forms. Examples are e.g. described in U.S. Pat. No. 7,376,237B2 [Westerkull; 2008] and in EP2403271 [Jinton; 2012].

The mixer 7 and the signal processor 8 together form a signal processing circuit, which is adapted to process at least one of the first and the second input audio signals to provide a processed audio signal, i.e. the modified audio signal.

The input audio spectrum analyser 11 is connected to receive the first and second digital input audio signals from the microphone 3 and the wireless receiver 6, respectively, and is adapted to repeatedly compute respective Fast Fourier Transformations (FFT) of each of these input audio signals to determine input audio spectra for each of the input audio signals.

The output audio spectrum analyser 12 is connected to receive the modified audio signal from the signal processor 8 and is adapted to repeatedly compute Fast Fourier Transformations (FFT) of the modified audio signal and apply the frequency responses of the power amplifier 9 and the vibrator 10 to determine output audio spectra of the audible signal provided to the user. The output audio spectrum analyser 12 may alternatively be connected to receive audio signals from one or more other components of the input means 3, 4, 5, 6, the signal processing circuit 7, 8 and/or the power amplifier 9, in which case the output audio spectrum analyser 12 may be required to apply further or other frequency responses and/or processing algorithms in order to correctly determine output audio spectra of the audible signal.

The first and second surface electrodes 13, 14 each constitute an outer surface portion of the housing 2. The surface electrodes 13, 14 are separate from each other and are arranged such that they abut the user's skin when the housing 2 is in the operating position. The surface electrodes 13, 14 are preferably arranged such that the length of the electric connection between the surface electrodes 13, 14 through the user's skin is as large as possible with the given housing 2 in the operating position. The surface electrodes 13, 14 may e.g. be arranged at opposite sides of the housing 2, and/or, in the case of an elongate housing 2, at opposite ends of the housing 2. The (two or more) surface electrodes are adapted to detect electric brain potentials of the individual (and located to be able to do so during operation of the hearing device, e.g. in a user's ear, e.g. in the user's ear canal). The use of surface electrodes located on the housing of an ear piece of a hearing device for picking up brainwave signals is e.g. described in US2010196861A1 [Lunner; 2010] and US2013101128A1 [Lunner & Neher; 2013].

The brainwave measurement circuit 15 is connected to receive electric signals from the first and second surface electrodes 13, 14 and is adapted to determine and provide electroencephalogram (EEG) signals in dependence on the electric signals. The brainwave measurement circuit 15 may comprise preamplifiers (not shown) adapted to amplify the electric signals and/or filters (not shown) adapted to emphasise EEG signal frequencies of particular of interest, e.g. the high-gamma frequency range.

The reconstructor 16 is connected to receive the EEG signals and is adapted to repeatedly reconstruct audio spectra from the one or more EEG signals. The reconstruction may e.g. be made using a reconstruction model as described in the article, "Reconstructing Speech from Human Auditory Cortex" by Pasley et al. (PLoS Biology, January 2012, Volume 10, Issue 1, e1001252). Preferably, a non-linear reconstruction model, such as a modulation model, is used. The use of such models is described in said article and in more detail in the documents referenced therein. Audio spectra reconstructed in dependence on EEG signals derived from a few surface electrodes arranged on, in or close to the ear of an individual cannot obtain the level of detail shown in said article. Nevertheless, the amount of information available in the audio spectra allows distinguishing between different sound sources and/or between different sound environments, given that these have different spectra. As is disclosed in the previously referenced article by Mesgarani and Chang, audio spectra reconstructed from EEG signals reflect the spectra of sounds that the user currently pays attention to, and in the following, these reconstructed audio spectra are referred to as attention audio spectra.

The output correlator 18 is connected to receive the output audio spectra and the attention audio spectra and is adapted to determine an output coherence between these audio spectra. The output coherence may thus be used as an indication of whether the user pays attention to the entire presented audible signal (high output coherence) or only to a part of the audible signal (low output coherence). The output correlator 18 preferably further determines those frequency ranges in which signals are present in the output audio spectra but not—or to lesser degree—in the attention audio spectra and provides an indication of the frequency ranges in an output difference signal.

The input correlator 17 is connected to receive the input audio spectra and is adapted to determine, for each of the input audio signals, an input coherence between the respective input audio spectra and the attention audio spectra. The input coherence for the first input audio signal may thus be used as an indication of the extent to which the user pays attention to the acoustic signal received by the microphone 3, and the input coherence for the second input audio signal may be used as an indication of the extent to which the user pays attention to the audio signal received by the wireless receiver 6. The input correlator 17 preferably further determines, for each of the input audio signals, those frequency ranges in which signals are present in the respective input audio spectra but not—or to lesser degree—in the attention audio spectra and provides an indication of the frequency ranges in a respective input difference signal.

The control unit 19 is connected to receive the output coherence and the output difference signal as well as the input coherences and the input difference signals for each of the input audio signals and is adapted to alter the processing in the signal processing circuit 7, 8 in dependence on one or more of the coherences.

The control unit 19 may monitor the output coherence and react to a decrease thereof by altering the processing such that the decrease is counteracted. The control unit 19 may alter the processing by altering a transfer function of the signal processing circuit 7, 8, preferably a transfer function of the signal processor 8. The control unit 19 may e.g. alter the transfer function such that it suppresses signals within one or more frequency ranges indicated in the output difference signal. Since the suppression of such frequency ranges makes the output audio spectra more similar to the attention audio spectra, provided that the user maintains attention to the same parts of the sound environment, it further causes an increase of the output coherence. Alternatively, the control unit 19 may set the transfer function to a predefined frequency characteristic, e.g. a frequency characteristic that is known to enhance speech signals in noisy environments. As a further alternative, the control unit 19 may set the transfer function to a predefined frequency characteristic known to enhance female speech or male speech if the attention audio spectra indicate that the user focuses attention respectively on a female speaker or a male speaker.

Alternatively, or additionally, the control unit 19 may alter the processing by altering the relative levels of the first and second digital input audio signals in the mixer 7. The control unit 19 may e.g. compare the input coherences for the first and the second digital input audio signals and control the mixer 7 to emphasise the particular input audio signal that has the highest input coherence. Similarly as described above, this makes the output audio spectra more similar to the attention audio spectra and thus causes an increase of the output coherence. Furthermore, sound sources only present in the suppressed one of the first and second digital input audio signals are removed from the audible signal, and thus, the input coherence for the emphasised one of the input audio signals is likely to increase. The degree of emphasis applied by the control unit 19 may depend on the difference between the input coherences in order to avoid altering in cases where it is unlikely that a change will increase the output coherence and/or the input coherences.

Alternatively, or additionally, the control unit 19 may alter the processing by altering an acoustic directivity pattern of the input means 3, 4, 5, 6. A directional microphone 3, e.g. a cardioid, a figure-eight or a hypercardioid microphone, may e.g. comprise two or more omnidirectional microphones, the outputs of which are combined as is already known in the art. The directivity pattern of such a directional microphone 3 may be altered by altering the levels, phases and/or time delays of the microphone signals to be combined. The input means may comprise several such directional microphones 3 with different directivity patterns using the output signals of the same two or more omnidirectional microphones. The outputs of these directional microphones 3 may each be amplified in a respective preamplifier 4 and digitised in a respective digitiser 5 to provide respective input audio signals. In this case, the acoustic directivity pattern may be altered by altering the relative levels of the input audio signals in the mixer 7 as described above. Alternatively, the directivity patterns may be altered by controlling how the output signals of the omnidirectional microphones are combined. In this case, the control unit 19 may follow e.g. a trial-and-error approach to determine which combination of the output signals of the omnidirectional microphones to use. As a further alternative, the directivity pattern may be set to a predefined pattern which emphasises acoustic signals arriving from the front, assuming that the user (as is usually the case) is focussing on sound sources in front of him or her.

Furthermore, the wireless receiver 6 may receive a microphone signal from an external microphone (not shown) located in the vicinity of the user, and in this case, in a wider sense, altering the relative levels in the mixer 7 also alters the acoustic directivity pattern of the input means 3, 4, 5, 6.

Instead of, or in addition to, monitoring the output coherence and react to a decrease thereof, the control unit 19 may monitor the input coherences for different input audio signals and, in dependence on a decrease of one or more of the input coherences, alter the processing as described above to emphasise the input audio signal with the highest input coherence. This may e.g. be of convenience when the hearing device 1 is a hearing aid and the user receives sound from an acoustically muted TV set through the wireless receiver and speech from a nearby person through the microphone. In this case, the hearing device 1 may automatically emphasise the sound source the user is focussing attention on.

The parameters of the reconstruction model may be determined based on measurements made on multiple individuals using an arrangement of measurement electrodes equal to or similar to the arrangement of the surface electrodes 13, 14 of the particular type of hearing device 1. A better performance of the reconstructor may be achieved by determining the reconstruction parameters based on measurements made on the individual intended to use the particular hearing device 1. In this case, the hearing device 1 itself is preferably used as a measurement instrument in a training session with the housing 2 in the operating position. In the training session, a range of different audible signals is presented to the user, preferably by means of the hearing device 1, and simultaneously, one or more EEG signals are determined from the electric signals received from the two or more surface electrodes 13, 14. Simultaneously or subsequently, output audio spectra of the audible signal are determined, and the EEG signals and the determined output audio spectra are input to the reconstruction model in order to train it to learn the relation between the EEG signals and the "true" output audio spectra. Obviously, the user should attempt to pay attention to the entire sound environment in the audible signals presented during the training session. In the training session, determining the output audio spectra of the audible signal and/or training the reconstruction model may be performed in and by the hearing device 1 itself or, partially or entirely, in a connected computer, e.g. in a fitting system for adapting other settings of the hearing device 1 to the needs of the user.

Ideally, the altering of the processing causes the audible signal to contain precisely those audio components that the user is interested in listening to, and the user may therefore continue listening without the stress of having to mentally remove or disregard disturbing signals. However, the altering may remove or suppress desired audio components, and/or the desired audio components may change in frequency content, direction or input source (microphone 3 or wireless receiver 6) after a processing alteration has been applied. In these cases, the user may attempt to focus on sound components only faintly present in the audible signal, which may cause the output coherence to decrease further. The control unit 19 may in some cases try to counteract this decrease by removing or suppressing further sound components, which may eventually lead the hearing device 1 into a deadlock in which no signal at all is presented to the user.

The reason for this is that the user cannot focus on sound components that are not present in the audible signal, and there is therefore no built-in mechanism to take back an applied suppression.

In order to avoid this deadlock, the control unit 19 may confine amplification changes caused by the processing alterations to remain within a predetermined range, e.g. ±10 dB, ±6 dB, ±3 dB or ±2 dB. Additionally, or alternatively, the control unit 19 may reverse a previously made processing alteration in dependence on a predetermined event. For instance, the control unit 19 may cancel suppression of frequency ranges and/or switch from a directional microphone 3 to an omnidirectional microphone 3. A suitable event may e.g. be that one or more of the input audio signals changes, e.g. as a result of the user moving to a different location. Examples of further suitable events are a change in one or more of the input audio spectra or a decrease of one or more of the input or output coherences. Furthermore, the control unit 19 may reverse the alteration in dependence on activation of a user control, i.e. a reset button, on the hearing device 1 or on a remote control and/or in dependence on expiry of a predetermined time period. The above described events may be combined arbitrarily.

The detection of decreases in the input and output coherences may comprise comparing the respective coherence with a corresponding threshold and/or determining a change rate of the respective coherence and comparing the change rate with a corresponding threshold. The control unit 19 may use the result of such comparisons to determine whether a decrease is large and/or fast enough to trigger an alteration of the processing.

Figure 2:
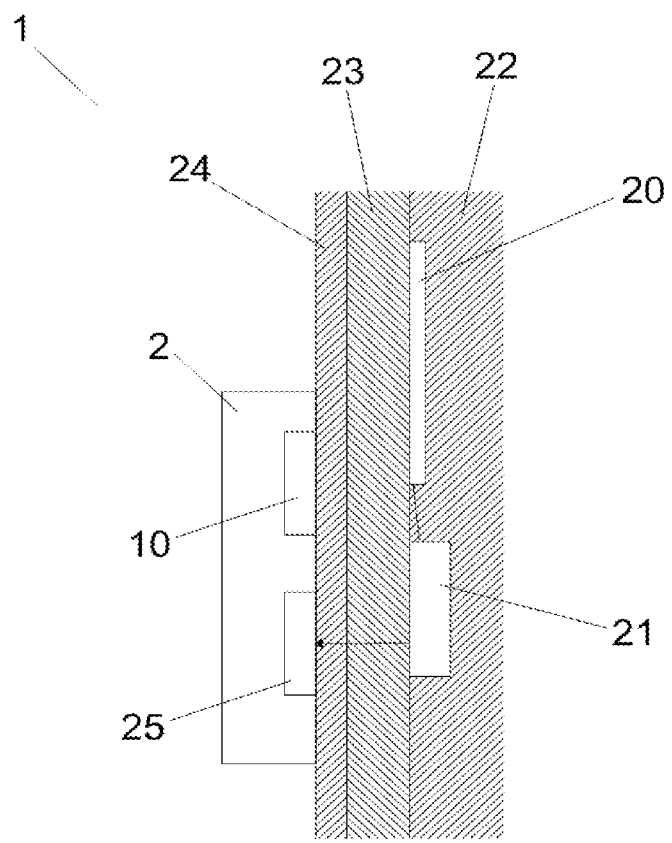
FIG. 2 shows a second embodiment of a hearing device according to the invention.

In a second embodiment of a hearing device, the (one, such as two, or more) surface electrode(s) adapted to detect electric brain potentials of the individual is(are) implanted in the individual's head instead of being implemented as surface electrode(s) as discussed above. The second embodiment of a hearing device 1 shown in FIG. 2 comprises a housing 2, a high-density electrode array 20, an EEG amplifier 21 and an EEG receiver 25. The electrode array 20 is implanted intracranially, i.e. in contact with brain tissue 22 inside the cranium 23 of the user. The EEG amplifier 21 is also implanted intracranially and connected to receive electric signals from the electrode array 20 and is adapted to amplify the electric signals and transmit the amplified electric signals through the cranium 23 and the skin 24 to the EEG receiver 25 in the housing 2. In the housing 2, the EEG receiver 25 is adapted to receive the transmitted signals and adapted to forward the received signals to a brainwave measurement circuit 15.

The electrode array 20, the EEG amplifier 21 and the EEG receiver 25 thus replace the surface electrodes 13, 14 of the first embodiment and also perform the same function, namely to convey electric signals depending on electric brain potentials to the brainwave measurement circuit 15. The housing 2 further comprises the components 3-12, 16-19 of the first embodiment, and the second embodiment thus functions essentially as the first embodiment. However, the implanted electrode array 20 allows the reconstructor 16 of the second embodiment to reconstruct the attention audio spectra with much greater detail and accuracy than the reconstructor 16 of the first embodiment. The implanted electrode array 20 comprises at least two separate electrodes, but preferably comprises at least 9, 25, 64 or 100 electrodes arranged in two dimensions parallel to the surface of the brain tissue 22.

The signal transmission from the EEG amplifier 21 to the EEG receiver 25 may be made by wired or wireless means, and the power for the EEG amplifier 21 may be supplied by wire or wirelessly from a battery or an accumulator in the housing 2. Suitable methods and devices for signal transmission and power supply of implanted circuits are well known, e.g. from cochlear implant hearing aids.

In further embodiments, the vibrator 10 may be implanted in the middle ear and/or in the inner ear. In this case, the vibrator 10 may be adapted to provide a structure-borne acoustic signal to a middle-ear bone and/or to the cochlea. Alternatively, the vibrator 10 may be adapted to provide a liquid-borne acoustic signal to the cochlear liquid, e.g. through the oval window.

In further embodiments, the output means may comprise one or more output electrodes (not shown) instead of or in addition to the vibrator 10. The output electrodes may be implanted in the cochlea or on the inside of the skull bone 23 and may be adapted to provide electric signals to the hair cells of the cochlea, to one or more hearing nerves, to the auditory cortex 22 and/or to other parts of the cerebral cortex 22. Cochlear implant hearing devices comprising stimulation electrodes have been known in many years in a variety of configurations. Examples of such devices are e.g. described in U.S. Pat. No. 4,207,441 [Ricard et al.; 1980] and in U.S. Pat. No. 4,532,930 [Crosby et al.; 1985].

Instead of or in addition to a vibrator or one or more electrodes, the output transducer may comprise a loudspeaker for converting an electric signal to an acoustic stimulus.

In embodiments wherein one or more parts of the output means 10 are implanted, further hearing device parts may be implanted as well, and in the extreme case, all parts of the hearing device 1 may be implanted. In embodiments having implanted output electrodes, a common electrode array 20 may serve both as output electrodes and as input electrodes for the EEG amplifier 21. The function of each electrode in the array 20 may be electronically configurable in order to allow for optimising the electrode configuration to the user.

Dependent on the type and purpose of the hearing device 1 of any embodiment, components described above that are not required for the operation of the particular hearing device 1 may be omitted. For instance, components 11, 17 for determining the input coherences may be omitted if it is not desired to adaptively alter the emphasis of the input audio signals. Conversely, components 12, 18 for determining the output coherence may be omitted, e.g. if altering the emphasis of the input audio signals is the only desired adaptive alteration. A microphone 3, a preamplifier 4 and a digitiser 5 may be omitted, e.g. in a headset, and a wireless receiver 6 may be omitted e.g. in a hearing aid. In a wired headset, a wireless receiver 6 may be replaced by an electric receiver, e.g. a plain input terminal or an electric input buffer. A signal processor 8 may be omitted in hearing devices 1 that merely apply amplification to the input audio signal.

Any or all of the electrodes 13, 14, 20, as well as of the output electrodes, may comprise an electrically conductive polymer, thus allowing it/them to be resilient. Any or all of the electrodes 13, 14, 20, as well as of the output electrodes, may be covered by a material comprising graphene, or alternatively by a material comprising carbon and titanium, in order to achieve a biocompatible surface.

In any embodiment, the hearing device 1 may be adapted to communicate with a further hearing device 1 arranged to provide an audible signal to the respective other ear of the user. The hearing devices 1 may thus form a binaural hearing system and may exchange audio and/or control signals with each other and coordinate or synchronise the adaptive alterations made to the audible signals for the two ears in dependence on the exchanged signals. Such exchanged signals may e.g. comprise electric signals received from the electrodes 13, 14, 20, determined EEG signals, output audio spectra, input audio spectra, attention audio spectra, output difference signals, input difference signals, output coherences, input coherences and/or resulting alterations of the audio processing. The electrodes 13, 14, 20 may optionally be omitted in the further hearing device 1, in which case the further hearing device 1 may adapt its audio processing in dependence on signals received from the first hearing device 1.

The mixer 7, the signal processor 8, the spectrum analysers 11, 12, the reconstructor 16, the correlators 17, 18 and the control unit 19 are preferably implemented mainly as digital circuits operating in the discrete time domain, but any or all portions hereof may alternatively be implemented as analog circuits operating in the continuous time domain. The same applies to such portions of the wireless receiver 6, the brainwave measurement circuit 15, the EEG amplifier 21 and the EEG receiver 25 that may be implemented digitally. Such digital circuits may be implemented in any suitable combination of hardware, firmware and software and/or in any suitable combination of hardware units. Furthermore, any single hardware unit may execute the operations of several functional blocks in parallel or in interleaved sequence and/or in any suitable combination thereof.

A hearing device 1, which is adapted to be arranged (at least partly) on or at least partly implanted in an individual's head and comprises one, such as two or more electrodes 13, 14, 20 adapted to detect electric brain potentials of the individual, may be controlled using a method comprising: providing one or more input audio signals; processing at least one of said one or more input audio signals to provide a processed audio signal; providing an audible signal to the individual in dependence on the processed audio signal; determining one or more EEG signals from electric signals received from the one, such as two or more electrodes 13, 14, 20; repeatedly determining first audio spectra of at least one signal from the group of signals consisting of said one or more input audio signals and the audible signal; repeatedly reconstructing second audio spectra from the one or more EEG signals; repeatedly determining a first coherence between the first and the second audio spectra; and altering said processing in dependence on the first coherence.

The method may further comprise: in a training session wherein the one, such as two or more electrodes 13, 14, 20 are arranged to detect electric brain potentials of the individual, providing an audible signal to the individual; determining one or more EEG signals from electric signals received from the one, such as two or more electrodes 13, 14, 20; repeatedly determining fourth audio spectra of the audible signal; and determining reconstruction parameters in dependence on said one or more EEG signals and the fourth audio spectra, wherein said reconstruction is made using the reconstruction parameters.

Said processing may further be altered in a manner suited to increase the first coherence in dependence on the first coherence decreasing.

Figure 3A:
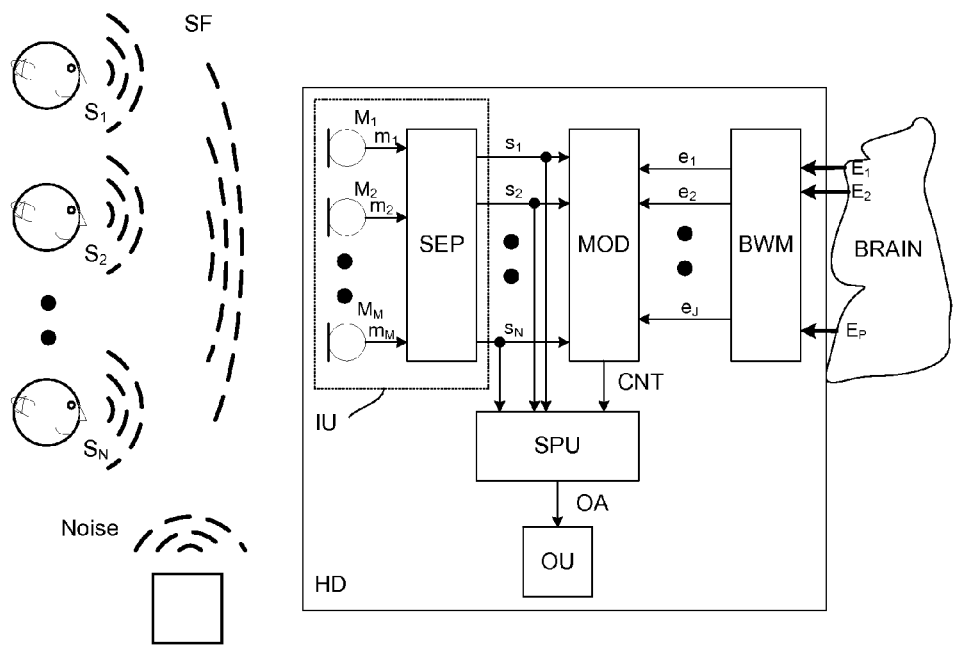
FIGS. 3A-3B shows a third and fourth embodiment of a hearing device according to the present disclosure.

FIG. 3 shows a third and fourth embodiment of a hearing device HD according to the present disclosure. FIG. 3A shows a situation where the sound field SF around the hearing device comprises N sound sources ($S_1, S_2, \ldots, S_N$), here speakers, and a noise source (Noise) representing other sounds in the environment than the N sound sources (speakers). The input unit IU of the hearing device HD comprises M microphones ($M_1, M_2, \ldots, M_M$) whose respective electric input signals ($m_1, m_2, \ldots, m_M$) are fed to an input processing unit comprising a weighting unit for combining the input signals and providing a number of output signals (e.g. comprising one or more directional microphone signals). In the present case the input processing unit comprises algorithms for source separation (and possibly noise reduction), as indicated by unit SEP that receives M electric input signals and provides as output N separated source signal $s_1$, $s_2, \ldots, s_N$, ideally representing the speech signals provided by the N speakers. The electric input signals $m_p$ (p= 1, 2, \ldots, M) and/or the source signals $s_i$ (i=1, 2, \ldots, N) may be time domain signals $s_i$ (t), e.g. in digitized form ($m_p[n]$, $s_i[n]$), where n is a time index. In other words, the input unit IU may comprise analogue to digital converting units for sampling (analogue electric) microphone input signals and providing digitized signals in the time domain. Additionally, the input unit IU may comprise time to time-frequency conversion units (e.g. (digital) Fourier transformation units (e.g. FFT, e.g. DFT) or (digital) filter banks) to provide each of the electric (microphone) input signals $m_p$ (or weighted combinations thereof) and/or separated source signals $s_i$ in a time frequency representation ($m_p[n,k]$ and $s_i[n,k]$, respectively), where k is a frequency index. Preferably, the time to time-frequency conversion units may be configurable, to allow activation or deactivation of one or more, such as all, time to time-frequency units, and/or partial activation (e.g. to allow analysis of only pre-selected frequency bands). In an embodiment, the model unit MOD is configurable. In an embodiment, the model unit MOD is configured to work in the time domain in a first specific mode of operation (e.g. a normal mode) and in the (time-) frequency domain in a second specific mode of operation (e.g. in a learning mode), where analysis of signal spectra are enabled. The hearing device (e.g. the model unit MOD) may preferably comprise voice activity detectors (e.g. applied to the electric input signals from the microphones and/or to the separated source signals) to detect periods of time where the signals in question comprise a speech signal component (and where not). The voice activity detectors may work in the time domain (on the full band signal) or, alternatively, in the time-frequency domain allowing the speech, or no-speech detection to be performed on a frequency band level. Thereby certain frequency bands and time periods of the input audio signals can be to be selected and ignored, respectively, with regard to the similarity analysis with the brainwave signals (thus reducing the complexity/power/time consumption of the calculations). The separated source signals $s_i$ are received by the model unit (MOD) and compared with (each of the or selected) brainwave signals (e.g. EEG signals) ($e_1, e_2, \ldots, e_J$) provided by the brainwave measurement unit BWM based on brainwave potentials picked up by the electrodes ($E_1, E_2, \ldots, E_P$) to determine their similarity. In an embodiment, the number of brainwave signals J is equal to the number of electrodes P. Alternatively, the number of brainwave signals J is smaller than the number of electrodes P, e.g. because some of the electrode potentials are judged to be (currently) irrelevant (e.g. because a variation of the measured potential is below a predefined threshold value). The model unit MOD preferably analyses each of the source signals $s_i$ vis-à-vis each of the brainwave signals $e_j$ and provides resulting similarity measures for each source signal and provides one or more resulting control signals CNT indicative of a target signal currently preferred by the user. The hearing device HD further comprises a signal processing unit SPU receiving the source signals $s_i$ from the input unit IU and the one or more control signals CNT from the model unit MOD. The signal processing unit SPU possibly performs further processing of the input source signals (e.g. the currently selected target signal), possibly mixing the currently selected target signal with one or more of the other input signals, and/or applying further noise reduction and/or compression algorithms, etc., to the signal(s), and providing at least one output signal OA. The output signal(s) OA is/are fed to an output unit OU for being presented to a user and perceived as sound (and/or for being transmitted to another device). The output unit may comprise one or more of a loudspeaker of an air conduction hearing device, a vibrator of a bone anchored hearing device, electrodes of a cochlear implant hearing device, and a wired or wireless transmitter.

Figure 3B:
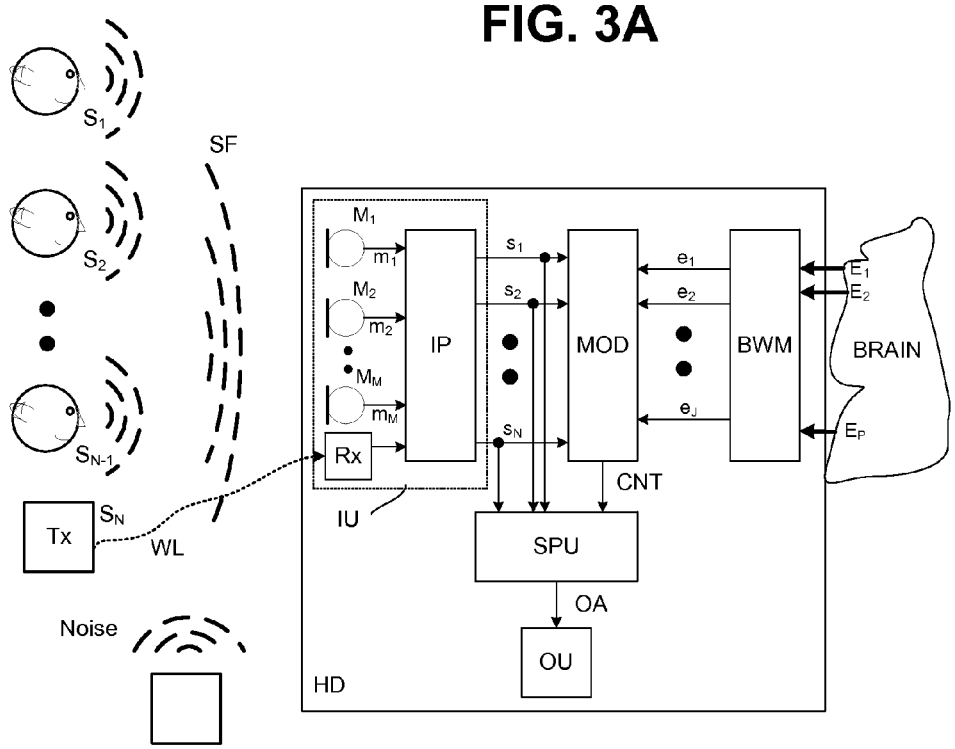

FIG. 3B shows a similar scenario as in FIG. 3A, but where (at least) one of the N speech sources ($S_N$) is transmitted via a wireless link WL from a device (e.g. a microphone) comprising a transmitter Tx and is received by the hearing device HD by wireless receiver Rx. Thus, (at least) one of the source signals ($s_N$) represents the wirelessly transmitted signal from sound source $S_N$.

In the embodiment of FIG. 3B, more than one (such as two or more, such as a majority or all) of the sound sources may be transmitted to the hearing device via wired or wireless connections (links, e.g. based on Bluetooth). In the latter case, the sound separation in the hearing device may be largely dispensed with (because the received signals are themselves (relatively) 'clean'). The hearing device may in an embodiment comprise no microphone, but be configured to directly receive all source signals, e.g. in digitized form (e.g. in a time-frequency representation). In his case, the hearing device may be configured to select a preferred one (or a preferred combination) of the directly received input audio signals by comparison with the concurrently recorded brainwave signals.

An important feature of a reliably functioning hearing device according to the present disclosure is the provision of good independent estimators of each single audio source for the correlator or model units to be able to choose which audio source the user currently wishes to focus on. To be able to make a good correlation/similarity measure between the audio input and the brainwave signals (e.g. EEG), it is necessary to have a good estimate of each of the separate audio sources alone.

A typical situation, where such a system might be utilized is in a 'cocktail party situation' comprising a number of speech sources where. A participant typically scans the 'auditory scene' (and in that situation needs inputs from all directions, as e.g. provided by so called omnidirectional (microphones)). When a hearing aid user wants to focus on one particular source, the other sources should be attenuated (this is what the brain does for a normally hearing person, and what we would like to simulate with the present invention.)

A typical application in a hearing device would be to have two or more directional microphones (e.g. with a fixed polar pattern or a steerable (adaptive) polar pattern) that have their respective directivity maximum pointing towards the different audio source(s) (e.g. the most powerful ones, or the ones in front of the user, etc.). The input from these directional microphones can be added to form an 'omnidirectional' input to listen to for the hearing aid user and added together to an omnidirectional pattern. In an embodiment, the hearing device comprises a mixture of directional and omnidirectional input audio signals. In an embodiment, the hearing device is configured to switch from an ordinary omnidirectional microphone to the target directional microphone. The brainwave (e.g. EEG) signal is then used to correlate/ estimate which of the sources is attended to and switches to the given directional microphone.

An alternative to using directional microphones could be to have locally placed microphones close to the target speakers and transmit the audio source signal to the hearing device provided with corresponding wireless receivers (that could for example be solved by wireless microphones and Bluetooth communication), to get as good as possible estimate of the single audio source.

In an embodiment, the hearing device comprises a user interface, e.g. an activation element (e.g. a button) on the hearing device or a wireless interface to a remote control (e.g. a special RC device or another electronic device, e.g. a SmartPhone, comprising an APP for performing such function). In an embodiment, the hearing device is configured to activate or deactive the use of the brainwave signals to influence the processing of the audio input signal(s) via the user interface. In an embodiment, the hearing device is configured to initiate—via the user interface—a determination of the similarity measure to identify target signal that the user is currently most likely to wish to listen to. In an embodiment, the hearing device is configured to be in a number of distinct modes of operation, e.g. entered automatically or entered via the user interface. In an embodiment, one of the distinct modes of operation of the hearing device is a learning mode, where the hearing device (in particular e.g. a causal model of the transfer function of an input audio signal to a brain wave signal) is trained on a number of different voices (to provide that the model is better suited for identifying such voices in a sound field comprising a mixture of voices (and possibly other (e.g. noise) sounds). Preferably, the model is trained on a particular voice (that is denoted the target input audio signal), e.g. alone and/or in a sound field comprising a mixture of the target voice and one or more other voices, and/or possibly additional noise at different levels. In such training mode, the user is aware that he or she is supposed to focus on the target voice. In an embodiment, one of the distinct modes of operation of the hearing device is a first normal mode of operation, where it is assumed that the hearing device has been trained to one or more voices. In an embodiment, one of the distinct modes of operation of the hearing device is a second normal mode of operation, where it is assumed that NO learning mode has preceded the second normal mode. In an embodiment, the analysis of the degree of similarity of the input audio signals and the brainwave signals is performed in the time frequency domain, when the hearing device is in the learning mode. In an embodiment, the analysis of the degree of similarity of the input audio signals and the brainwave signals is performed in the time domain, when the hearing device is in the first normal mode. In an embodiment, the analysis of the degree of similarity of the input audio signals and the brainwave signals is performed in the time frequency domain, when the hearing device is in the second normal mode.

Figure 4:
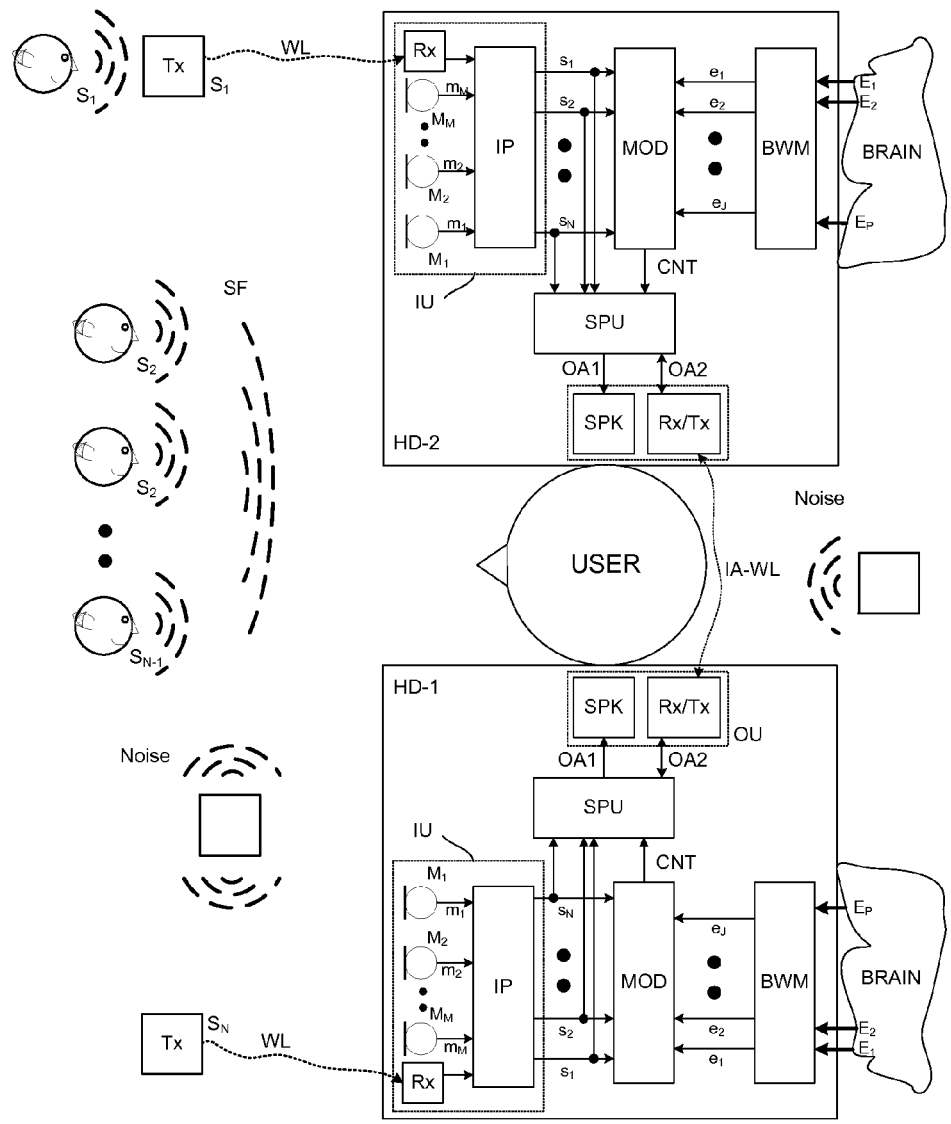
FIG. 4 shows an embodiment of a binaural hearing system comprising first and second hearing devices according to the present disclosure.

FIG. 4 shows an embodiment of a binaural hearing system comprising first (HD-1, left) and second (HD-2, right) hearing devices according to the present disclosure. The first and second hearing devices may e.g. be embodied in the exemplary embodiments shown in FIG. 3 (or may be embodied in the exemplary embodiments of FIG. 1 or 2). In addition to the functional elements described in connection with FIG. 3, the first and second hearing devices of FIG. 4 comprises antenna and transceiver circuitry (Rx/Tx) configured to establish a wireless link IA-WL between the two hearing devices. In this scenario, signals from some common sources ($S_2$-$S_{N-1}$) are received by both hearing devices (HD-1, HD-2) and, additionally, signals from some sources ($S_N$) are received only by the first hearing device (HD-1) on the left side and from some ($S_1$) only by the second hearing device (HD-2) on the right side of the head of the user. The common signals are in this case acoustically propagated signals from speakers ($S_2$-$S_{N-1}$) mixed together with noise sources (Noise), here located in front and to the rear of the user, to a common sound field SF that is received by microphones M; of the two hearing devices (but where a particular wavefront from an individual sound source may have a different time of arrival and level, etc., at corresponding microphones of the first and second hearing devices). The 'different' signals are the wirelessly propagated (streamed) signals from sound sources $S_1$ and $S_N$. These sound source signals are transmitted from transmitting devices (e.g. a microphone (as $S_1$) or e.g. from a telephone or an entertainment device, e.g. a TV (as $S_N$)) via wireless links WL. The wireless links can be of any kind, and e.g. be defined by a standardized or proprietary interface. Only one wireless signal is indicated to be received at each hearing device, but the first and second hearing devices could be provided with two or more different streamed signals (via different input sources, TV, cellphone, Internet, . . . ). In an embodiment, the majority or all sound sources ($S_1$ to $S_N$) are wirelessly received by one or both hearing devices (this could e.g. be signals from a number of wireless microphones). The binaural hearing system of FIG. 4 is configured to exchange audio signals (e.g. one or more of source signals $s_1$-$s_N$) and control signals (CNT), represented by signal OA2, between the two hearing devices via antenna and transceiver circuitry (Rx/Tx) configured to establish a wireless link IA-WL. This allows the system to be configured to identify which of the currently received signals—be it acoustically propagated or wirelessly received signals—that the user wishes to focus on (e.g. music from an entertainment device or speech from a TV or telephone audio input). In an embodiment, the system is configured to identify which of the currently, wirelessly received signals, the user wishes to focus on. This signal may e.g. be mixed with one or more of the other sound source signals (the latter possibly at a lower level relative to the identified 'wished' signal) and presented to the user.

Figure 5:
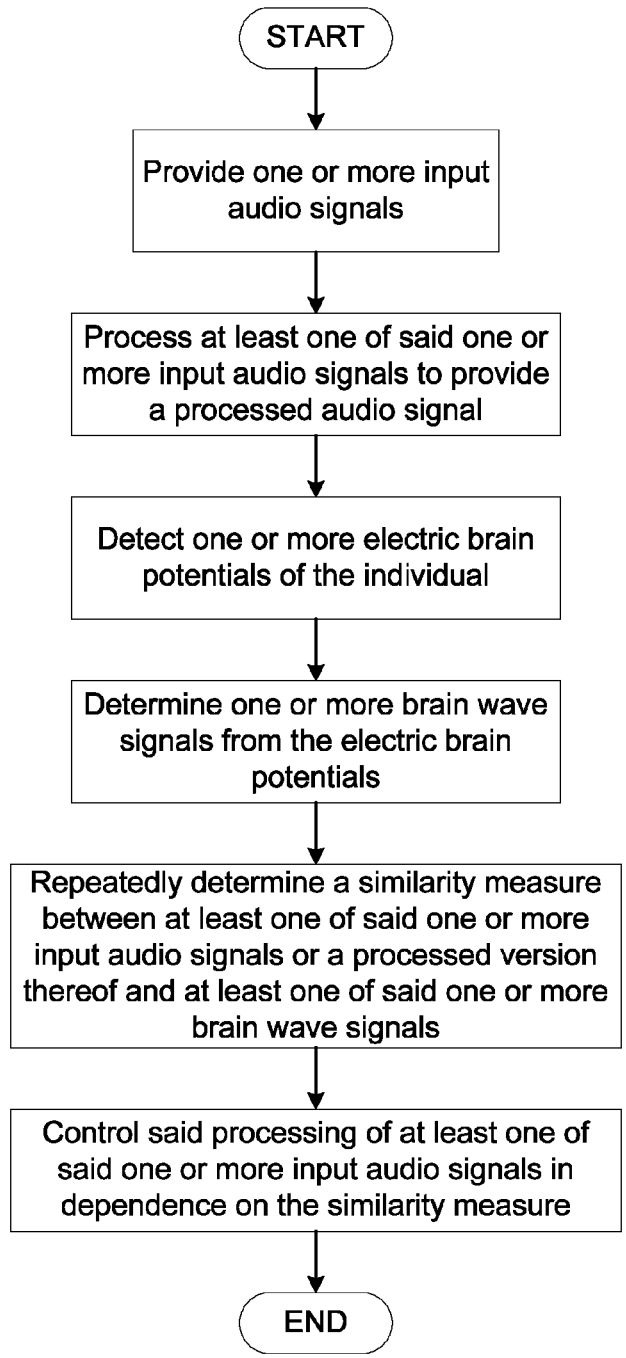
FIG. 5 shows a flow diagram of a method of operating a hearing device.

FIG. 5 shows a flow diagram of a method of operating a hearing device. The method comprises:
  providing one or more input audio signals;
  processing at least one of said one or more input audio signals to provide a processed audio signal;
  detecting one or more electric brain potentials of the individual;
  determine one or more brainwave signals from the electric brain potentials;
  repeatedly determining a similarity measure between at least one of said one or more input audio signals or a processed version thereof and at least one of said one or more brainwave signals; and
  controlling said processing of at least one of said one or more input audio signals in dependence on the similarity measure.

A typical goal of the control of the processing is to identify the input audio signal that has the highest probability of being a target signal for the individual wearing the hearing device.

Figure 6:
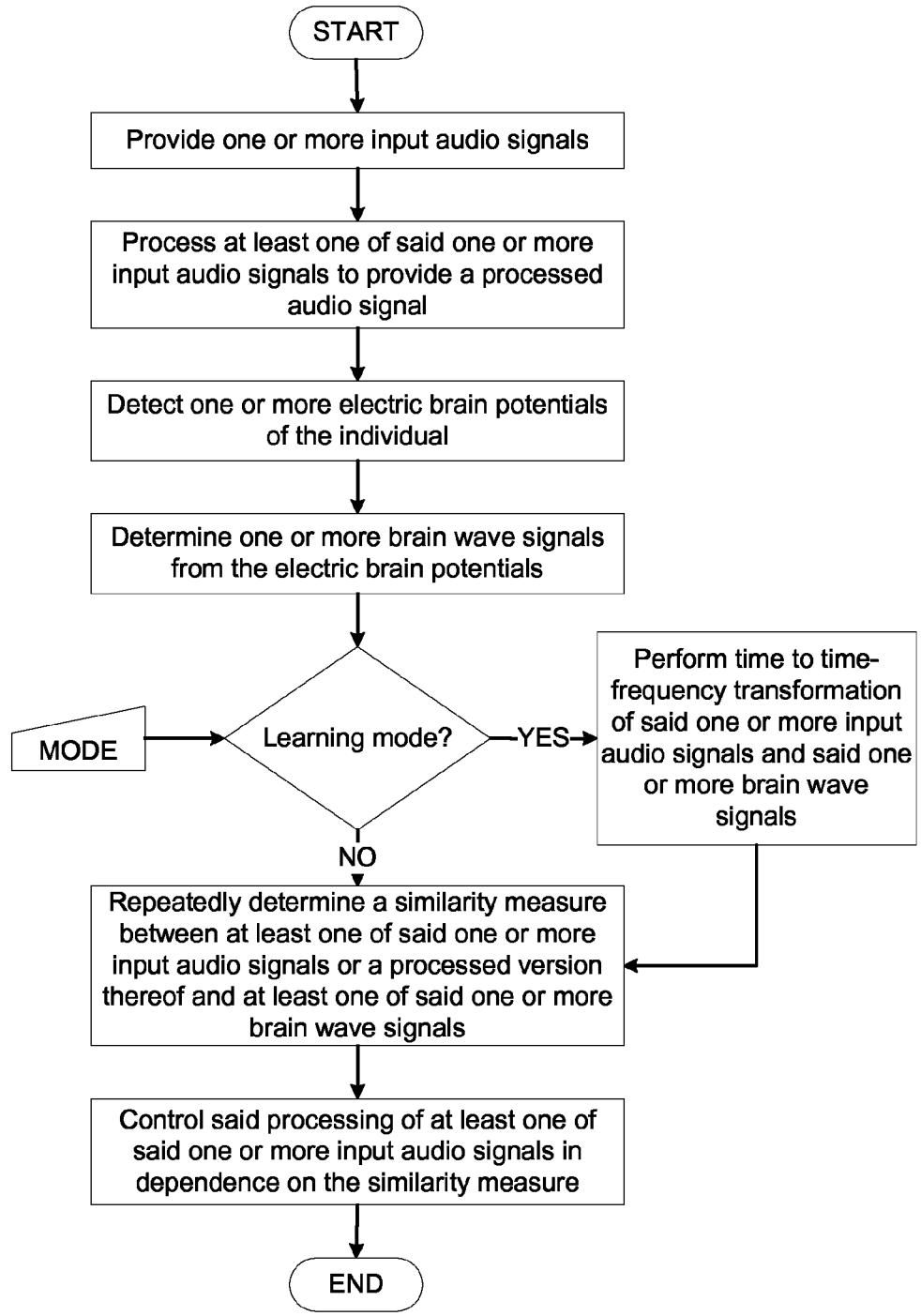
FIG. 6 shows a flow diagram of an embodiment of a method of operating a hearing device.

FIG. 6 shows a flow diagram of an embodiment of a method of operating a hearing device, the embodiment comprising the steps illustrated in FIG. 5, but which furthermore comprises a learning mode, wherein a target signal is known (agreed on with the user in advance of activating the method).

The method comprises providing a mode input identifying whether or not the hearing device is in a learning mode. If the mode input indicates that a learning mode is entered, the (time dependent) input audio signals and the brainwave signals that are to be compared for identifying a degree of similarity are converted to the frequency domain before determining a similarity measure. If the mode input indicates that a learning mode is NOT entered, the similarity measure for determining a degree of similarity between the input audio signals and the brainwave signals is determined in the time domain. This has the advantage of reducing the complexity of the calculations in a normal mode of operation.

Further modifications obvious to the skilled person may be made to the disclosed method, system and/or device without deviating from the scope of the invention. Within this description, any such modifications are mentioned in a non-limiting way.

Some preferred embodiments have been described in the foregoing, but it should be stressed that the invention is not limited to these, but may be embodied in other ways within the subject-matter defined in the following claims. For example, the features of the described embodiments may be combined arbitrarily, e.g. in order to adapt the system, the devices and/or the method according to the invention to specific requirements.

It is further intended that the structural features of the system and/or devices described above, in the detailed description of 'mode(s) for carrying out the invention' and in the claims can be combined with the methods, when appropriately substituted by a corresponding process. Embodiments of the methods have the same advantages as the corresponding systems and/or devices.

Any reference numerals and names in the claims are intended to be non-limiting for their scope.

The invention claimed is:

1. A hearing device adapted to be arranged on or at least partly implanted in an individual's head and comprising:
    an input unit providing one or more input audio signals in an audible frequency range;
    a signal processing circuit adapted to process at least one of said one or more input audio signals to provide a processed audio signal;
    an output unit adapted to provide an audible signal to the individual in dependence on the processed audio signal;
    one or more electrodes adapted to detect electric brain potentials of the individual;
    a brainwave measurement circuit adapted to determine one or more EEG signals from electric signals received from the one or more electrodes;
    a first spectrum analyzer adapted to repeatedly determine first spectra in the audible frequency range of at least one signal from the group of signals consisting of said one or more input audio signals and the audible signal;
    a reconstructor adapted to repeatedly reconstruct second spectra in the audible frequency range from the one or more EEG signals;
    a first coherence calculation unit adapted to repeatedly determine a first coherence between the first and the second spectra; and
    a control unit adapted to alter said processing in dependence on the first coherence.

2. A hearing device according to claim 1, wherein the reconstructor is adapted to reconstruct the second spectra using reconstruction parameters determined during a preceding training session.

3. A hearing device according to claim 1, wherein the control unit is adapted to alter said processing in a manner suited to counteract a detected decrease in the first coherence.

4. A hearing device according to claim 1 and further comprising:
    a second spectrum analyser adapted to repeatedly determine third spectra in the audible frequency range of at least one further signal from said group of signals; and
    a second coherence calculation unit adapted to repeatedly determine a second coherence between the second and the third spectra,
    wherein the control unit is adapted to alter said processing in dependence on the first and the second coherence.

5. A hearing device according to claim 4, wherein the control unit is adapted to alter said processing in a manner suited to increase the second coherence in dependence on the first coherence decreasing.

6. A hearing device according to claim 1, wherein the control unit is adapted to alter said processing by altering a transfer function of the signal processing circuit.

7. A hearing device according to claim 1, wherein the input unit comprises at least one input transducer arranged to receive an acoustic signal from the individual's surroundings and adapted to provide at least one of said one or more input audio signals in dependence on the acoustic signal.

8. A hearing device according to claim 7, wherein the at least one input transducer comprises at least one directional microphone, and wherein the control unit is adapted to alter said processing by altering an acoustic directivity pattern of the input unit.

9. A hearing device according to claim 1, and further adapted to confine amplification changes caused by said processing alterations to remain within a predetermined range.

10. A hearing device according to claim 1, wherein the control unit is adapted to reverse a previously made processing alteration in dependence on a predetermined event.

11. A hearing device according to claim 10, wherein said predetermined event comprises at least one of a change in said one or more input audio signals, a change in the second spectra, a decrease of the first coherence, a change in the third spectra, a decrease of the second coherence, activation of a user control and expiry of a predetermined time period.

12. A hearing device according to claim 1, wherein the input unit comprises a wired or wireless receiver adapted to provide at least one of said one or more input audio signal in dependence on a wireless or wired signal received from a further device.

13. A hearing device according to claim 1 wherein the output unit comprises one or more of a vibrator, a loudspeaker, and one or more electrodes.

14. A method for controlling a hearing device adapted to be arranged on or at least partly implanted in an individual's head and comprising one or more electrodes adapted to detect electric brain potentials of the individual, the method comprising:
    providing one or more input audio signals in an audible frequency range;

processing at least one of said one or more input audio signals to provide a processed audio signal;

providing an audible signal to the individual in dependence on the processed audio signal;

determining one or more EEG signals from electric signals received from the one or more electrodes;

repeatedly determining first spectra in the audible frequency range of at least one signal from the group of signals consisting of said one or more input audio signals and the audible signal;

repeatedly reconstructing second spectra in the audible frequency range from the one or more EEG signals;

repeatedly calculating with a coherence calculation unit a first coherence between the first and the second spectra; and altering said processing in dependence on the first coherence.

15. A method according to claim 14 and further comprising:

in a training session wherein the one or more electrodes are arranged to detect electric brain potentials of the individual, providing a training audible signal to the individual;

determining one or more EEG signals from electric signals received from the one or more electrodes;

repeatedly determining fourth spectra in the audible frequency range of the training audible signal; and determining reconstruction parameters in dependence on said one or more EEG signals and the fourth spectra, wherein said reconstruction is made using the reconstruction parameters.

16. A method according to claim 14 wherein said processing is altered in a manner suited to increase the first coherence in dependence on the first coherence decreasing.

17. A hearing device configured to be arranged at least partly on an individual's head or at least partly implanted in an individual's head and comprising:

an input unit providing one or more input audio signals in an audible frequency range;

a signal processing circuit adapted to process at least one of said one or more input audio signals to provide a processed audio signal;

one or more electrodes adapted to detect electric brain potentials of the individual; and a brainwave measurement circuit adapted to determine one or more brainwave signals from electric signals received from the electrode(s);

a model unit adapted to repeatedly determine a causal model providing a similarity measure indicating a degree of similarity of at least one of said one or more input audio signals or a processed version thereof and at least one of said one or more brainwave signals; and a control unit adapted to alter said processing in dependence on the similarity measure, wherein the causal model is a model of the transfer of an input audio signal to a brainwave signal and comprises a transfer function $$H(q) = \frac{B(q)}{A(q)} = \frac{b_0 + b_1 q^{-1} + \ldots + b_n q^{-n}}{1 + a_1 q^{-1} + \ldots + a_n q^{-n}}$$

where $q^{-1}$ denotes the shift operator.

18. A hearing device according to claim 17 wherein the causal model has a memory optimized to the individual wearing the hearing device.

19. A hearing device according to claim 17, comprising:

a first spectrum analyser configured to repeatedly determine first spectra in the audible frequency range of at least one signal from the group of signals consisting of said one or more input audio signals and the processed audio signal, and a reconstructor configured to repeatedly reconstruct second spectra in the audible frequency range from the one or more brainwave signals, and wherein the model unit is adapted to repeatedly determine the similarity measure between the first and second audio spectra.

20. A hearing device according to claim 17 comprising one or more voice activity detectors applied to one or more of the input audio signals to detect periods of time, where the signals in question comprise a speech signal component and where not.

21. A binaural hearing system comprising a first and second hearing assistance device according to claim 17 and configured to establish a communication link between the first and second hearing devices to provide that data can be exchanged or forwarded from one to the other.

22. A method of operating a hearing device configured to be worn by an individual, the method comprising:

providing one or more input audio signals;

processing at least one of said one or more input audio signals to provide a processed audio signal;

detecting one or more electric brain potentials of the individual;

determine one or more brainwave signals from the electric brain potentials;

repeatedly determining a causal model providing a similarity measure between at least one of said one or more input audio signals or a processed version thereof and at least one of said one or more brainwave signals; and controlling said processing of at least one of said one or more input audio signals in dependence on the similarity measure, wherein the causal model is a model of the transfer of an input audio signal to a brainwave signal and comprises a transfer function $$H(q) = \frac{B(q)}{A(q)} = \frac{b_0 + b_1 q^{-1} + \ldots + b_n q^{-n}}{1 + a_1 q^{-1} + \ldots + a_n q^{-n}}$$

where $q^{-1}$ denotes the shift operator.

23. A method according to claim 22 wherein the controlling said processing comprises at least one of identifying the input audio signal that has the highest probability of being a target signal for the individual wearing the hearing device; and identifying an input audio signal that has a low probability of being a target signal for the individual wearing the hearing device.

24. A method according to claim 21, further comprising:

providing a learning mode, wherein a target signal is known and agreed on with the individual in advance of activating the method.

25. A method according to claim 24, wherein the causal model is trained during a training phase, where the learning mode is activated.

26. A method according to claim 21 wherein the similarity measure is determined by analysis of the input audio signals and the brainwave signals in the (time-) frequency domain in the learning mode, and wherein the similarity measure is determined by analysis in the time domain in a normal mode of operation of the hearing device.

27. A hearing device according to claim 1 wherein the reconstructor adapted to repeatedly reconstruct second audio spectra from the one or more EEG signals comprises a non-linear reconstruction model.

28. A hearing device according to claim 27 comprising a modulation model.

29. A method according to claim 14 wherein the repeated reconstruction is based on a non-linear reconstruction model.

30. A hearing device according to claim 19 wherein the reconstructor adapted to repeatedly reconstruct second audio spectra from the one or more EEG signals comprises a non-linear reconstruction model.

31. A hearing device according to claim 30 comprising a modulation model.

32. A hearing device according to claim 1 comprising a hearing aid, a listening device, an active ear-protection device, an earphone or a headset.

33. A hearing device according to claim 17 comprising a hearing aid, a listening device, an active ear-protection device, an earphone or a headset.

34. The hearing device according to claim 20, wherein the voice activity detectors detect frequency bands where the signals in question comprise a speech signal component and where not.

* * * * *